United States Patent [19]

Nishimura et al.

[11] Patent Number: 4,936,998
[45] Date of Patent: Jun. 26, 1990

[54] FILTER MEDIUM FOR SELECTIVELY REMOVING LEUCOCYTES

[75] Inventors: Takao Nishimura; Yoshiyuki Mizoguchi, both of Oita, Japan

[73] Assignee: Asahi Medical Co., Ltd., Tokyo, Japan

[21] Appl. No.: 138,374

[22] PCT Filed: Mar. 28, 1987

[86] PCT No.: PCT/JP87/00194

§ 371 Date: Nov. 27, 1987

§ 102(e) Date: Nov. 27, 1987

[87] PCT Pub. No.: WO87/05812

PCT Pub. Date: Oct. 8, 1987

[30] Foreign Application Priority Data

Mar. 28, 1986 [JP] Japan ................... 61-68580

[51] Int. Cl.$^5$ ............................. B01D 39/16
[52] U.S. Cl. ......................... 210/638; 210/496; 210/502.1; 210/508; 210/660; 210/767
[58] Field of Search ............ 210/502.1, 505, 506, 210/507, 508, 509, 660, 679, 767, 807, 638, 649, 496

[56] References Cited

U.S. PATENT DOCUMENTS

| | | |
|---|---|---|
| 4,330,410 | 5/1982 | Takenaka et al. ............ 210/767 |
| 4,416,777 | 11/1983 | Kuroda et al. ............... 210/508 |
| 4,617,124 | 10/1986 | Pall et al. .................... 210/508 |
| 4,620,932 | 11/1986 | Howery ....................... 210/505 |
| 4,701,267 | 10/1987 | Watanabe et al. ........... 210/505 |

FOREIGN PATENT DOCUMENTS

55-129755 10/1980 Japan .
59-203565 11/1984 Japan .
60-119955 6/1985 Japan .
60-119956 6/1985 Japan .
60-119957 6/1985 Japan .
61-48373 3/1986 Japan .
61-48375 3/1986 Japan .
61-48376 3/1986 Japan .
61-226056 10/1986 Japan .
61-253071 11/1986 Japan .
2062498 5/1981 United Kingdom .

OTHER PUBLICATIONS

Biomaterials, vol. 6, Nov. 1985, pp. 409–415, Butterworth & Co., GB, N. Yui et al., "Reversibility of Granulocyte Adhesion Using Polyamine-grafted Nylon-6 as a New Column Substrate for Granulocyte Separation".
Derwent Abstract 85-193,172, "Synthetic High Polymer for Artificial Organs Production".
Chemical Abstracts, vol. 97, No. 2, Jul. 12, 1982, p. 365, K. Sanui et al, "Effect of Microphase Separated Structure in Platelets Adhesion on Graft Polyamides".

*Primary Examiner*—W. Gary Jones
*Attorney, Agent, or Firm*—Birch, Stewart, Kolasch & Birch

[57] ABSTRACT

There is disclosed a filter medium for selectively removing leucocytes, which is composed of fibers, each containing nonionic hydrophilic groups and nitrogen-containing basic functional groups at least in its peripheral surface portion. The present filter medium is useful for efficiently removing leucocytes while holding down the loss of platelets to a minimum and, therefore, the present filter medium can be effectively utilized in platelet transfusions and extracorporeal circulation leucocyte removal therapies and the like.

26 Claims, 1 Drawing Sheet

FILTER MEDIUM FOR SELECTIVELY REMOVING LEUCOCYTES

FIELD OF THE INVENTION

The present invention relates to a fibrous filter medium for selectively removing leucocytes. More particularly, the present invention is concerned with a filter medium for selectively removing leucocytes, which is capable of efficiently removing leucocytes, with little loss of platelets, from a cell-containing suspension containing both platelets and leucocytes, represented by blood. Still more particularly, the present invention is concerned with a filter medium which is used as a filter for selectively removing leucocytes, which is capable of removing leucocytes inevitably contained in the blood to be used for, e.g., platelet transfusion while holding down the loss of platelets to the minimum, and which is also capable of removing leucocytes in the extracorporeal circulation leucocyte removal therapy for autoimmune diseases and leukemia while holding down the loss of platelets to a minimum.

DESCRIPTION OF THE PRIOR ART

In the field of blood transfusion, platelet transfusion for improving the bleeding condition of a patient fills an important position. Platelet transfusion includes fresh whole blood transfusion, fresh concentrated red cells transfusion, platelet rich plasma transfusion and platelet concentrate transfusion, and in each type of such transfusions, the blood product usually contains a considerable amount of leucocytes. If a patient repeatedly receives transfusion of blood containing leucocytes, anti-leucocyte antibodies are likely to be produced in the patient. In such a patient, an antigen-antibody reaction occurs between the leucocytes transfused along with the transfused blood and the anti-leucocyte antibodies, causing side effects such as rigor, fever, headache and nausea. It is also known that in blood transfusions, if the transfusion blood contains a large amount of lymphocytes or if the immune system of the blood recipient is weakened for some reason, the so-called GVH reaction is likely to occur. Also, it is recently known that the less the amount of the leucocytes introduced in platelet transfusion, the better the survival of the transfused platelets in the body of the patient. For the above reasons, it has been desired in the field of platelet transfusion to remove leucocytes including lymphocytes as much as possible while holding down the loss of platelets to a minimum.

Meanwhile, the therapies for autoimmune disease and leukemia by extracorporeal circulation have recently been drawing attention as new therapies free from the danger of causing side effects which are often observed in pharmacotherapy. In this case too, of course, it is desired to effectively remove leucocytes including lymphocytes while holding down the loss of platelets to a minimum.

The leucocyte removal from the blood has conventionally been conducted by a centrifugation process using a continuous type centrifuge and the like. However, this process has disadvantages in that the efficiency of leucocyte removal is not so high, that the useful components of the blood including platelets are considerably lost, and that not only expensive apparatus are needed but also cumbersome operations are required.

On the other hand, there has been proposed a filtration process which consists in removing leucocytes by adhering leucocytes onto fibers. This filtration process has advantages in that the leucocyte removal efficiency is high, the loss of erythrocytes and plasma is low, and the operation required is simple and can generally be performed at low cost.

Takenaka et al. disclosed that a filter comprising a mass of fibers having an average diameter of 3 to 10 μm can efficiently entrap leucocytes (see U.S. Pat. No. 4,330,410, British Patent No. 2018151B, French Patent No. 7905629, and West German Patent No. 2908722). Watanabe et al. disclosed that a non-woven fabric filter comprised of fibers having an average diameter of less than 3 μm not only has a high leucocyte' removal efficiency but also can attain an increased rate of treating blood (see Japanese Patent Application Laid-open Specification No. 60-193468 and European Patent Application Publication No. 0155003). However, they do not contain a description with respect to the behavior of platelets, and according to the present inventors' actual experiments in which blood was flowed through these known filters, it was found that a considerable amount of platelet was also removed along with leucocytes.

Kuroda et al. disclosed a method for collecting a leucocyte- and lymphocyte- enriched blood containing less amounts of erythrocytes and platelets by the use of a filter comprising fibers coated with an antithrombotic material (see Japanese Patent Application Laid-open Specification No. 55-129755). However, according to the present inventors' actual experiment in which blood is flowed through this filter, although the loss of platelets was low, the ability to entrap leucocytes was low so that the selective removal of leucocytes could not be attained.

Tsuruta et al. disclosed that a polymer having nitrogen-containing basic functional groups and having a nitrogen content of from 0.05 to 3.5% by weight exhibits an extremely low adhering property for platelets (see Japanese Patent Application Laid-open Specification Nos. 60-119955 to 119957). However, this application does not contain a disclosure about the behavior of leucocytes for the above-mentioned polymer.

As described hereinbefore, there has so far not been known any method that is capable of selectively and efficiently removing leucocytes, with little loss of platelets, from a cell-containing suspension containing both platelets and leucocytes

DISCLOSURE OF THE INVENTION

An object of the present invention is to provide a filter medium useful for a filter for selectively removing leucocytes, which is capable of efficiently removing leucocytes while holding down the loss of platelets to a minimum and which is useful in a platelet transfusion and an extracorporeal circulation leucocyte removal therapy.

Not only in the case of a fiber, but also in general, the adhesiveness of cells to a certain material depends on the property of the surface of the material.

It is well known that in order to prevent platelets from adhering to a certain material, a hydrophilic monomer is graft-polymerized onto the surface of the material, or a hydrophilic polymer is coated on the surface of the material. However, the material surfaces obtained by such techniques become less adhesive not only to platelets but also to leucocytes and, therefore, such techniques have never been able to be employed to attain the object of the present invention, that is, provision of a filter medium for selectively removing leucocytes, which is capable of efficiently removing leucocytes by adhesion with little loss of platelets.

In the meantime, it has been a generally observed phenomenon that in a physiological liquid such as one containing cells, the surface of a material having nitrogen-containing basic functional groups turns to have a positive charge and becomes well adhesive to both platelets and leucocytes which have a negative charge.

The present inventors have made extensive and intensive studies with a view to developing a material for selectively adhering leucocytes, which is not adhesive to platelets but adhesive to leucocytes. As result, it has surprisingly been found that a fiber having nonionic hydrophilic groups and nitrogen-containing basic functional groups in its peripheral surface portion and having a basic nitrogen atom content of from 0.2 to 4.0% by weight in the surface portion, has such a property found in no conventional fibers that it is well adhesive to leucocytes while being less adhesive to platelets, and it has also been found that, by using this fiber as material for a filter medium, removal of leucocytes can efficiently be performed while holding down the loss of platelets to a minimum. Based on these novel findings, the present inventors have completed the present invention. That is, according to the present invention, there is provided a filter medium for selectively removing leucocytes, which comprises a plurality of fibers, each comprising a body portion and a peripheral surface portion, and each containing nonionic hydrophilic groups and nitrogen-containing basic functional groups at least in said peripheral surface portion, said peripheral surface portion having a basic nitrogen atom content of from 0.2 to 4.0% by weight.

The reasons for the employment of fibers in the filter medium of the present invention reside in that a fiber form has a large area per unit weight, which is ideal for efficiently removing leucocytes, and that fibers can easily be fabricated into a filter form.

The filter medium of the present invention comprises a plurality of fibers, each of which comprises a body portion and a peripheral surface portion, and at least the peripheral surface portion (hereinafter often referred to as "surface portion") comprises a substance containing nonionic hydrophilic groups and nitrogen-containing basic functional groups. In other words, with respect to each of the fibers to be used in the filter medium of the present invention, the body portion and the peripheral surface portion may be either not integrally or integrally formed, and a portion which is comprised of the above-mentioned portion may be either only the peripheral surface portion, or not only the peripheral surface portion but also the body portion, i.e., the entire fiber. Further, it is not critical whether or not the surfaces of both ends of each fiber, which are included by the body portion of the fiber, are comprised of the above-mentioned substance.

Examples of nonionic hydrophilic groups in the present invention include hydroxyl groups and amido groups. Examples of nitrogen-containing basic functional groups in the present invention include a primary amino group, a secondary amino group, a tertiary amino group, and a quaternary ammonium group, and also include nitrogen-containing aromatic ring groups such as a pyridyl group and an imidazolyl group.

The term "basic nitrogen atom" used herein means a nitrogen atom in the above-mentioned nitrogen-containing basic functional groups, and in the filter medium of the present invention it is requisite that the portion which contains nonionic hydrophilic groups and nitrogen-containing basic functional groups have a basic nitrogen atom content of from 0.2 to 4.0% by weight. If the basic nitrogen atom content is less than 0.2% by weight, the filter medium becomes less adhesive not only to platelets but also to leucocytes, thereby rendering it impossible to selectively remove leucocytes. On the other hand, if the basic nitrogen atom content is more than 4.0% by weight, the filter medium becomes adhesive not only to leucocytes but also to platelets, thus rendering it impossible for leucocytes to be selectively removed. The more preferable range of the basic nitrogen atom content is from 0.3 to 1.5% by weight. With respect to the most suitable contents of the basic nitrogen atoms in various raw materials for the filter medium of the present invention, which are described later, they vary according to the types of the functional groups contained in these raw materials and the conditions under which the filter medium would be used (e.g. they vary heavily depending on the type of an anticoagulant to be added to blood). Various types of anticoagulants may be employed, but there may preferably be used citric acid type anti-coagulants [ACD (acid-citrate-dextrose), CPD (citrate-phosphate-dextrose)] and the like, because they stabilize platelets so that a smooth passage of platelets through a filter is facilitated. When heparin is used as an anticoagulant, filtration of a small amount of blood through a small-sized filter in a short period of time exhibits no problem, but filtration of a large amount of blood by a largesized filter is likely to activate platelets, so that it becomes difficult for the platelets to pass through the filter.

In the present invention, the molar amount of the nonionic hydrophilic group, in terms of the molar amount of hydroxyl group, amido group, or ethylene oxide unit in polyethylene oxide chains, may preferably be at least equal to, more preferably at least three times as large as the molar amount of the basic nitrogen atom.

The amount of the nitrogen-containing basic functional groups and the amount of the nonionic hydrophilic groups, and the basic nitrogen atom content can be measured by known methods such as an infrared absorptiometric method using a multiple total reflection infrared spectrometer, and elementary analysis.

With respect to the fibers of the filter medium of the present invention, the average fiber diameter is preferably 10 $\mu$m or less, more preferably less than 3 $\mu$m, since the smaller the averager fiber diameter, the larger the leucocyte removing ability per unit weight of the fiber. However, if the average fiber diameter is less than 0.3 $\mu$m, the filter made up of the fibers is not only likely to be clogged, and but also likely to damage the cell wall of erythrocytes, causing hemolysis. Therefore, the average fiber diameter is preferably 0.3 $\mu$m or more. In this connection, from the viewpoints of the leucocyte removing ability etc., fibers having an average diameter of from 0.5 to 2.0 $\mu$m are most preferred.

The "fiber diameter" used herein is defined by the formula:

$$x = 2\sqrt{\frac{1}{\pi} \cdot \frac{W}{\rho \cdot l}} \cdot 10^4$$

wherein x is a diameter of the fiber in $\mu$m, W is a weight of the fiber in g, $\rho$ is a density of the fiber in g/cm$^3$, and l is a length of the fiber in cm. The average fiber diameter means the value obtained by averaging the diameters of fibers.

In using the filter medium of the present invention as a leucocyte removing filter, it may be used in the form of a simple mass of fibers or in the form of a woven or non-woven fabric. However, the woven or non-woven fabric form is preferable because with this form, in general, the leucocyte removing performance per unit weight of the filter is high and, in addition, the filter thickness in the direction of the filtration flow can be reduced, so that the pressure loss may be reduced, enabling the blood processing rate to be increased with advantages. Further, in the viewpoint of ease in manufacturing (particularly when the fiber diameter is small), the non-woven fabric form is most preferably employed.

As described before, with respect to each of the fibers used in the filter medium of the present invention, as long as the peripheral surface portion of the fiber is made of a substance containing nonionic hydrophilic groups and nitrogen-containing basic functional groups such as those described before, the fiber structure may be either such that the body portion of the fiber is comprised of a substance which is different in chemical composition from that of the peripheral surface portion, or such that the entire fiber is comprised of a substance containing nonionic hydrophilic groups and nitrogen-containing basic functional groups such as those described before. But, from the viewpoints of ease in manufacturing and cost in production, etc., the former is preferable. FIG. 1 is a diagrammatic cross section of the fiber in the case of the former. Surface portion 1 and body portion 2 have different chemical compositions, and the thickness of surface portion 1, actually, is small as to be almost negligible as compared to the fiber diameter. As mentioned before, in the present invention, it is requisite that surface portion 1 have a specific chemical composition in which nonionic hydrophilic groups and nitrogen-containing basic functional groups are contained, and the content of the basic nitrogen atom is from 0.2 to 4.0% by weight. From the viewpoints of technical ease and total production cost, it is preferred that body portion 2 be first prepared using a later-mentioned general purpose polymer material such as one used for producing a common fiber, and then surface portion 1 having the above-mentioned specific chemical composition be formed thereon. This is more advantageous than the method in which the entire fiber is prepared using the above-mentioned specific chemical composition so that the entire fiber has a uniform structure of the above-mentioned specific chemical composition.

Illustratively stated, in the case where the body portion and peripheral surface portion of the fiber are formed integrally with each other, if the entire fiber is to contain nonionic hydrophilic groups and nitrogen-containing basic functional groups and have a basic nitrogen atom content of from 0.2 to 4.0% by weight, the fiber can be prepared by spinning a polymer produced by the polymerization of later-mentioned monomers. In addition, it is noted that even the fiber having its peripheral surface portion formed integrally with its body portion may have a similar structure to that of FIG. 1 in which surface portion 1 having the above-mentioned specific chemical composition is formed on the peripheral surface of body portion 2. That is, the fiber having such structure may be obtained by a method in which the surface portion of body portion 2 is modified into a substance having the above-mentioned specific chemical composition by, e.g., chemical treatment, ultraviolet ray radiation or low temperature plasma treatment, or a method in which a polymer layer having the above-mentioned specific chemical composition is formed on body portion 2 by surface graft polymerization.

On the other hand, where the peripheral surface portion is formed separately from the body portion, there may be employed a method in which a polymer material containing nonionic hydrophilic groups and nitrogen-containing basic functional groups and having a basic nitrogen atom content of from 0.2 to 4.0% by weight is coated on a fiber material constituting the body portion. This coating method is preferable since it can be generally adopted irrespective of the type of the material of body portion 2. This coating method is also preferable since even if the surface portion of body portion 2 is physically or chemically non-uniform, surface portion 1 having the above-mentioned specific chemical composition can be stably formed thereon. The diagrammatic cross section of the fiber obtained by the above coating method can also be represented by FIG. 1.

As the material for the body portion, there may be employed any of known fibers. Examples of such fibers include synthetic fibers such as polyester fibers, polyamide fibers, polyacrylonitrile fibers, polymethylmethacrylate fibers, polyethylene fibers and polypropylene fibers, semi-synthetic fibers such as cellulose acetate fibers, regenerated fibers such as cuprammonium rayon fibers, viscose rayon fibers, and viscose staple fibers, natural fibers such as cotton fibers, silk and wool, inorganic fibers such as glass fibers and carbon fibers. Of these, synthetic fibers are preferably employed. When a fiber which is produced by spinning is to be employed, a fiber which can easily be spinned, of course, is preferred from the viewpoint of ease in manufacturing.

The surface portion containing hydrophilic groups and nitrogen-containing basic functional groups may preferably have an average thickness of about 10 Å or more. If the thickness is less than 10 Å, it becomes difficult for the body portion to be completely covered by a substance containing nonionic hydrophilic groups and nitrogen-containing basic functional groups, so that it becomes difficult to selectively remove leucocytes while holding down the loss of platelets to a minimum. There is particularly no upper limit for the average thickness. However, when a polymer containing nonionic hydrophilic groups and nitrogen-containing basic functional groups is coated on the body portion or when the peripheral surface portion is formed by graft polymerization, the upper limit for the average thickness of the polymer coating or the graft polymerized peripheral surface portion is preferably less than about 1 μm. If the average thickness is 1 μm or more, the cost for the formation of the peripheral surface portion made of polymer becomes high and, a portion of the surface portion is likely to come off and enter the blood to be processed when the mechanical strength of the formed peripheral surface portion is low. The more preferable range of the average thickness of the peripheral surface portion is from 40 Å to 400 Å.

When peripheral surface portion 1 containing nonionic hydrophilic groups and nitrogen-containing basic functional groups and having a basic nitrogen atom content of from 0.2 to 4.0% by weight is formed on the surface of body portion 2 by surface graft polymerization or polymer coating, there is generally employed a method in which one or more monomers having nonionic hydrophilic groups and one or more monomers having nitrogen-containing basic functional groups are subjected to customary surface graft polymerization, or a method in which a polymer produced by polymerizing the above-mentioned two types of monomers by a usual procedure is coated. With respect to the method for synthesizing a coating material, different types of monomers may be graft copolymerized or block copolymerized, and when the thus obtained coating material is coated on fibers constituting a body portion, there can be formed a microphase separated structure in the peripheral surface portion. Alternatively, there may be employed a method in which a polymer having nonionic hydrophilic groups and a polymer having nitrogen-containing basic functional groups are separately prepared and these two types of polymers are blended just before coating.

Examples of monomers containing nonionic hydrophilic groups which are employable for the above-mentioned graft polymerization or for the synthesis of a polymer for the above-mentioned coating method, includes monomers containing a hydroxyl group or an amido group, such as 2-hydroxyethyl (meth)acrylate, 2-hydroxypropyl (meth)acrylate, vinyl alcohol (vinyl acetate is polymerized and then hydrolyzed), (meth)acrylamide and N-vinylpyrrolidone. Examples of nonionic hydrophilic groups also include a polyethylene oxide chain. Of the above-mentioned monomers, 2-hydroxyethyl acrylate and 2-hydroxyethyl methacrylate are preferably employed from the viewpoints of availability, ease in handling in the polymerization, performance of the resulting surface portion when blood is flowed.

Examples of monomers containing nitrogen-containing basic functional groups include allylamine; (meth)acrylic acid derivatives such as dimethylaminoethyl (meth)acrylate, diethylaminoethyl (meth)acrylate, dimethylaminopropyl (meth)acrylate, 3-dimethylamino-2-hydroxypropyl (meth)acrylate; styrene derivatives such as p-dimethylaminomethylstyrene, p-diethylaminoethylstyrene; vinyl derivatives of nitrogen-containing aromatic compounds such as 2-vinylpyridine, 4-vinylpyridine, 4-vinylimidazole; and derivatives as obtained by converting the above-mentioned vinyl compounds to a quaternary ammonium salt using a halogenated alkyl or the like. Of these monomers, dimethylaminoethyl (meth)acrylate and diethylaminomethyl (meth)acrylate are preferably employed from the viewpoints of availability, ease in handing in the polymerization, performance of the resulting surface portion when blood is flowed.

In producing the filter medium of the present invention by a method in which the above-mentioned type of polymer material is coated on fibers constituting the body portion, the fiber may be dipped in a solution prepared by dissolving the polymer material in a suitable solvent, and then surplus solution is removed by, e.g., mechanical compression, gravity or centrifugation, followed by drying in dry gas or under vacuum at room temperature or at elevated temperatures.

Before coating, the surface of the fiber may be treated with appropriate chemicals, in order to facilitate the adhesion between the polymer material and the fiber. Further, after the coating, the polymer-coated fiber may be subjected to heat treatment, in order to enhance the adhesion between the fiber and the above-mentioned polymer material or to cause a crosslinking reaction in the coated polymer material for stabilizing the surface portion. In addition, the coating may be conducted simultaneously with, or after the spinning of the fiber. Further, in the case where the filter medium of the present invention is to be used as a filter for removing leucocytes in the form of a woven or non-woven fabric, the coating of the above-mentioned polymer material may be conducted before or after the fabrication of the fibers into the woven or nonwoven fabric form.

When the filter medium of the present invention is employed as a filter for removing leucocytes, the filter medium of the present invention may be packed in a known appropriate filter container for blood filtration which has an inlet and an outlet. The bulk density of the packed filter medium may be varied according to the fiber diameter, but is preferably 0.02 to 0.7 g/cm$^3$. The "bulk density" used herein means a value obtained by dividing the weight of the effective portion of the filter medium packed in a container by the volume of space occupied by the effective portion. When the filter medium of the present invention is used in the form of a woven or non-woven fabric, it may be used as a single sheet of fabric or as a laminate of a plurality of sheets of fabrics depending on the thickness of the sheet. When a laminate of a plurality of sheets is used, the number of sheets is not strictly limited but is usually several to several tens depending on the blood filtration conditions.

PREFERRED EMBODIMENT OF THE INVENTION

The present invention will be described in more detail with reference to the Examples, which should not be construed to be limiting the scope of the present invention.

Examples 1 to 3 and Comparative Examples 1 to 4

A copolymer of 2-hydroxyethyl methacrylate (hereinafter referred to as "HEMA") and diethylaminoethyl methacrylate (hereinafter referred to as "DEAMA") was synthesized by a customary solution radical polymerization. With respect to the polymerization conditions, the polymerization was conducted at 60° C. for 8 hours, using monomers at a monomer concentration of 1 mole/l in ethanol in the presence of 1/200 mole/l of azoisobutylonitrile (AIBN) as an initiator. The thus obtained polymer was subjected to elementary analysis thereby to determine its basic nitrogen atom content. A non-woven fabric (weight : 60 g/m$^2$) of polyethylene terephthalate fibers having an average diameter of 1.8 $\mu$m was cut into disks of 25 mm in diameter and these disks were dipped in a 0.1% ethanol solution of the above obtained copolymer, and the surplus of the solution contained in the disks was removed by squeezing. The resultant disks were held in filter holders by two disks per holder and dried by blowing dry air.

The thus obtained coated disks of fabric were set in filter holders (manufactured by Shibata Scientific Technology Ltd., Japan) by two disks per holder to form a filter (thickness, 1.0 mm), and 5 ml of fresh bovine blood, having incorporated therein ACD (acid-citrate-dextrose) as anticoagulant, was flowed through the filter by means of a syringe pump at a constant flow rate of 2 ml/min at room temperature.

Certain amounts of the blood before and after filtration were taken as samples. A blood sample was diluted with Türk's solution and then subjected to a measurement of the leucocyte concentration by using a hemocytometer. At the same time, another blood sample was diluted 100 times with a 1% aqueous ammonium oxalate solution and subjected to a measurement of the platelet concentration by using a hemocytometer (Brecher-Cronkite method). Leucocyte removal ratio and platelet passage ratio were determined by the following equations.

Leucocyte removal ratio (%) =

$$\left\{1 - \frac{\text{Leucocyte concentration after passage through non-woven fabric}}{\text{Leucocyte concentration before passage through non-woven fabric}}\right\} \times 100$$

Platelet passage ratio (%) =

$$\frac{\text{Platelet concentration after passage through non-woven fabric}}{\text{Platelet concentration before passage through non-woven fabric}} \times 100$$

In Table 1, there are shown the DEAMA unit content (mole %) and the basic nitrogen atom content (% by weight) in the coated copolymer of HEMA and DEAMA, the value of leucocyte removal ratio and the value of platelet passage ratio.

The non-coated filter medium (Comparative Example 4) corresponds to the filter disclosed by Watanabe et al. and the filter medium coated with a polymer containing 0% of DEAMA (i.e. the homo-polymer of HEMA) (Comparative Example 1) corresponds to the filter disclosed by Kuroda et al.

For a filter medium for selectively removing leucocytes with high efficiency and with little loss of platelets, it is practically necessary that the platelet passage ratio be 75% or more and the leucocyte removal ratio be 85% or more.

As apparent from Table 1, in the case of the non-coated filter (the filter of Watanabe et al.) (Comparative Example 4), the leucocyte removal ratio is 88.8%, which is satisfactorily high, but the platelet passage ratio is as low as only 12.9%, that is, selective removal of leucocytes cannot be attained. On the other hand, in the case of the filter coated with the homopolymer of HEMA (the filter of Kuroda et al.) (Comparative Example 1), the platelet passage ratio is satisfactorily 77.0%, but the leucocyte removal ratio is as low as 68.3%, that is, in this case too, selective removal of leucocytes is not attained.

As indicated in Table 1, even in the case where a material containing nonionic hydrophilic groups and nitrogen-containing basic functional groups is used for coating, if the basic nitrogen atom content is low (Comparative Example 2), the platelet passage ratio is as high as 91.6%, but the leucocyte removal ratio is as low as 66.3%, that is, selective removal of leucocytes cannot be attained, whereas if the basic nitrogen atom content is 7.56% which is too high, and the nonionic hydrophilic group content is zero (Comparative Example 3), the leucocyte removal ratio is sufficiently 98.1%, but the platelet passage ratio is as low as 3.2%, that is, in this case too, selective removal of leucocytes is not attained.

In contrast, in the case of each of the filter mediums which have basic nitrogen atom contents of 0.53%, 1.03% and 1.98%, respectively, a leucocyte removal ratio of 85% or more is attained while enjoying a platelet passage ratio of 75% or more, that is, selective removal of leucocytes is performed.

TABLE 1

| | Comparative Example 1 | Comparative Example 2 | Example 1 | Example 2 | Example 3 | Comparative Example 3 | Comparative Example 4 |
|---|---|---|---|---|---|---|---|
| DEAMA content (mole %) | 0 | 1 | 5 | 10 | 20 | 100 | Non-coated |
| Nitrogen atom content (wt %) | 0 | 0.11 | 0.53 | 1.03 | 1.98 | 7.56 | (0) |
| Leucocyte removal ratio (%) | 68.3 | 66.3 | 94.8 | 96.7 | 98.6 | 98.1 | 88.8 |
| Platelet passage ratio (%) | 77.0 | 91.6 | 88.2 | 78.8 | 76.4 | 3.2 | 12.9 |

Leucocyte concentration before filtration 7430 cells/μl
Platelet concentration before filtration 147000 cells/μl

EXAMPLES 4 to 6

A copolymer of HEMA and ethyl trimethylmethacrylate ammonium chloride having an ethyl trimethylmethacrylate ammonium chloride monomeric unit content of 5 mole % (the basic nitrogen atom content is 0.52 wt% and the copolymer is hereinafter referred to as "HT"), a copolymer of HEMA, N-vinylpyrrolidone and dimethylaminomethyl methacrylate, in which the contents of the monomeric units are 60 mole %, 30 mole % and 10 mole %, respectively (the basic nitrogen atom content is 1.10 wt% and the copolymer is hereinafter referred to as "HVM"), a copolymer of HEMA, monomethoxy polyethylene glycol methacrylate (the number of the repeating units of ethylene oxide : 23) and DEAMA, in which the contents of the monomeric units are 80 mole %, 5 mole % and 15 mole %, respectively (the basic nitrogen atom content is 1.12 wt% and the copolymer is hereinafter referred to as "HME") were each synthesized by solution polymerization in the same manner as in Example 1. Each of the thus obtained copolymers was coated on a non-woven fabric in the same manner as in Example 1, thereby to obtain filter mediums, and these filter mediums were set in filter holders as described in Example 1, and then bovine blood was flowed through these filter mediums, in order to examine the permeabilities to blood cells.

The results are shown in Table 2. Each of the filter mediums coated with HT, HVM and HME, respectively was found to be a filter medium which is capable of selectively removing leucocytes with a leucocyte removal ratio of 85% or more and a platelet passage ratio of 75% or more.

TABLE 2

|  | Example 4 H T | Example 5 H V M | Example 6 H M E |
|---|---|---|---|
| Basic nitrogen atom content (wt %) | 0.52 | 1.10 | 1.12 |
| Leucocyte removal ratio (%) | 95.4 | 93.8 | 92.3 |
| Platelet passage ratio (%) | 80.7 | 83.9 | 85.1 |

Leucocyte concentration before filtration: 5470 cells/μl
Platelet concentration before filtration: 273000 cells/μl

EXAMPLE 7

The same non-woven fabric as used in Example 1 was dipped in a 1:1 mixture of N,N-diethylethylenediamine and methanol, thereby to introduce, by ester-amide exchange reaction, amide groups, and hydroxyl groups derived from the ester groups of the polyethylene terephthalate of the non-woven fabric, as nonionic hydrophilic groups, and diethylamino groups as nitrogen-containing basic functional groups onto the surface of the non-woven fabric. The reaction formula is as follows.

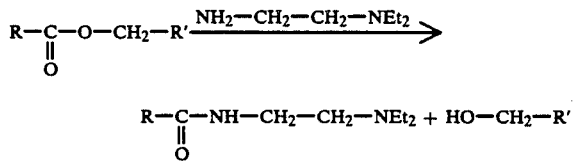

The analysis of the surfaces of the fibers by means of a multiple total reflection infrared spectrometer showed that the ratio of the ester linkages to the amido linkages was about 9:1 and the basic nitrogen atom content was about 1.3% by weight.

This non-woven fabric with its surface chemically treated was cut into a disk of 25 mm in diameter to obtain a filter, and blood was flowed therethrough in the same manner as in Example 1 (leucocyte concentration before filtration : 5740 cells/μl, platelet concentration before filtration : 258000 cells/μl).

With respect to the results, the leucocyte removal ratio was 86.5% and the platelet passage ratio was 81.0%, that is, leucocytes were selectively removed.

EXAMPLE 8 AND COMPARATIVE EXAMPLE 5

The same non-woven fabric as used in Example 1 was cut into squares each having a 67 mm×67 mm size, and 20 of them were compiled into a laminate, which was then packed in a column as indicated in FIG. 2. In FIG. 2 non-woven fabric laminate 6 is set in column 3 composed of 2 square frame works 4 and 440 and the peripheral portion of the laminate is firmly pressed together. Numerals 5 and 5' represent projections which are provided inside the column, and which hold the non-woven fabric filter at points in its portion other than the periphery. The non-woven fabric filter has an effective cross-sectional area of 60 mm×60 mm=3600 mm² and has a thickness of 7 mm. A 0.1% polymer solution in ethanol in which the polymer is a copolymer of HEMA and DEAMA and has a DEAMA unit content of 5 mole% (the basic nitrogen atom content is 0.53 wt%, and the polymer is hereinafter referred to as "HE-5") was flowed through the above-mentioned column having set therein the above-mentioned non-woven fabric, and the fabric set in the column was subsequently dried by blowing dry air and further well dried in vacuum.

2 Liters of fresh bovine blood having incorporated therein anticoagulant ACD was flowed through the thus prepared column at a flow rate of 30 ml/min, at 37° C. in order to examine the leucocyte removal ratio and the platelet passage ratio (the concentrations of leucocytes and platelets before filtration were 5800 cells/μl and 315000 cells/μl, respectively) (Example 8). For comparison, a filter medium not coated with HE-5 was also examined under the same conditions as mentioned above (Comparative Example 5).

The non-coated filter (the filter of Watanabe et al.) exhibited a leucocyte removal ratio of 78.6% and a platelet passage ratio of 78.2% while the filter coated with HE-5 (the filter of the present invention) (Example 8) exhibited a leucocyte removal ratio of 89.3% and a platelet passage ratio of 91.4%. In the case of the non-coated filter, when blood is flowed therethrough in an amount as much as 2 liters, platelets tend to pass therethrough relatively easily, however, the leucocyte removal ratio becomes decreased, so that selective removal of leucocytes cannot be satisfactorily performed. On the other hand, in the case of the filter coated with HE-5, even when such a large amount of blood is flowed, satisfactorily selective removal of leucocytes can be performed. This indicates that the filter medium of the present invention can apply to a leucocyte removal therapy by the extracorporeal circulation method.

EXAMPLE 9

A non-woven fabric made of polyethylene terephthalate fibers having an average diameter of 4.7 μm (weight : 88 g/m²) was cut into squares each having a 67 mm×67 mm size and 14 of them were packed in columns in the same manner as in Example 8, followed by subjecting to coating treatment with HE-5. When 400 ml of fresh bovine blood (leucocyte concentration : 4830 cells/μl, platelet concentration : 284000 cells/μl) was flowed through the thus obtained filter in the same manner as in Example 8, there were obtained a leucocyte removal ratio of 86.1% and a platelet passage ratio of 92.3%, that is, selective removal of leucocytes was performed.

Example 10 and Comparative Example 6

The same non-woven fabric as used in Example 1 was cut into squares each having a 67 mm×67 mm size and 12 of them were compiled into a laminate, which was then packed in a column and subjecting to coating with HE-5 polymer in the same manner as in Example 8. 500 ml of platelet rich plasma (leucocyte concentration : 413 cells/μl, platelet concentration : 299000 cells/μl) prepared by centrifuging fresh bovine blood having incorporated therein ACD was flowed through the above obtained column by the force of gravity at a head of 80 cm (Example 10). For comparison, a non-coated filter medium was also examined under the same conditions as mentioned above (Comparative Example 6).

The non-coated filter exhibited a leucocyte removal ratio as high as 100% but a platelet passage ratio as low as 69.7%, whereas the filter coated with HE-5 exhibited a leucocyte removal ratio of 100% and a platelet passage ratio of 93.8%, that is, leucocytes were selectively removed with little loss of platelets.

Example 11 and Comparative Example 7

The same non-woven fabric as used in Example 1 was cut into disks each having a diameter of 70 mm and 8 of them were compiled into a laminate, which was then packed in a column so that the column filter has an effective cross-sectional area of 28.3 cm$^2$ and a thickness of 4 mm, and subsequently subjected to coating with HE-5 polymer in the same manner as in Example 8. 300 ml of platelet concentrate (leucocyte concentration : 4675 cells/μl, platelet concentration : 550000 cells/μl) prepared by centrifuging fresh bovine blood having incorporated therein ACD was flowed through the above obtained column by the force of gravity at a head of 80 cm (Example 11). For comparison, a non-coated filter medium was also examined under the same conditions as mentioned above (Comparative Example 7).

The non-coated filter exhibited a leucocyte removal ratio as high as 93.1%, but a platelet passage ratio as low as 60.5%, whereas the filter coated with HE-5 exhibited a leucocyte removal ratio of 92.0% and a platelet passage ratio of 88.1%, which are both high, that is, leucocytes were selectively removed with little loss of platelets.

Probability of Utilization in Industry

Figure 1:
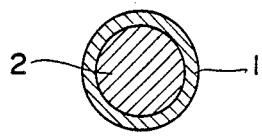
FIG. 1 is a diagrammatic cross-sectional view of a fiber used for the filter medium of the present invention, which comprises a peripheral surface portion and a body portion having a different chemical composition from that of the peripheral surface portion. 1 : peripheral surface portion of the fiber 2 : body portion of the fiber
Figure 2:
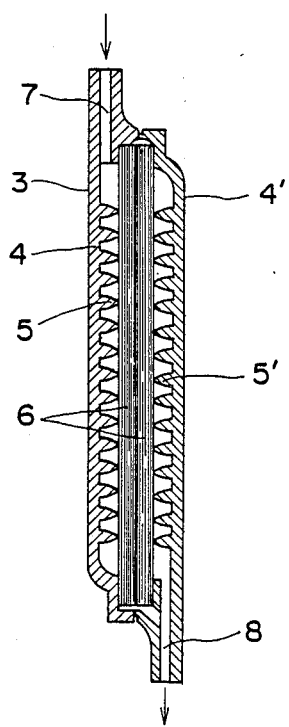
FIG. 2 is a cross-sectional side view of one form of a filter (column) having packed therein a filter medium of the present invention. 3 : column body 4, 4' : square-shaped frames 5, 5' : projections 6 : non-woven fabric filter layer 7 : blood inlet 8: blood outlet

The filter medium of the present invention is extremely useful for selectively removing leucocytes with high efficiency and with little loss of platelets. It is expected that by the removal of leucocytes contained in a blood product for platelet transfusions by using the filter medium of the present invention, the side effects due to the transfusions will be reduced and, further, the life of transfused platelets would be prolonged. It is further expected that when the filter medium of the present invention is employed in an extracorporeal circulation leucocyte removal therapy for patients of autoimmune diseases and leukemia, leucocytes would be removed efficiently in a shortened period of time and almost no other useful blood components would be lost and, hence, the burden on the patient would be little, providing an excellent remedial effect.

What is claimed is:

1. A method for selectively removing leukocytes from a suspension containing leucocytes and platelets, comprising:
    contacting a suspension containing leucocytes and platelets with a filter medium,
    said filter medium comprising a plurality of fibers, each comprising a body portion and a peripheral surface portion, at least said peripheral surface portion of which comprises a polymer obtained by polymerization of at least one vinyl monomer having a nonionic hydrophilic group with at least one vinyl monomer having a nitrogen-containing basic functional group and has a basic nitrogen atom content of from 0.2 to 4.0% by weight,
    thereby causing said leucocytes to selectively adhere to said filter medium while allowing the resultant platelet-enriched suspension substantially free of leucocytes to pass through said filter medium, and
    collecting said platelet-enriched suspension, and wherein said collected platelet-enriched suspension is adapted to be used for platelet transfusion or to be returned to a donor of said suspension containing leucocytes and platelets for performing extracorporeal leucocyte removal therapy.

2. The method according to claim 1, wherein the basic nitrogen atom content of said peripheral surface portion is from 0.2 to 1.5% by weight.

3. The method according to claim 1, wherein the average fiber diameter is from 10 μm or less.

4. The method according to claim 3, wherein the average fiber diameter is from 0.3 μm to less than 3.0 μm.

5. The method according to claim 1, wherein said filter medium is in the form of a non-woven fabric.

6. The method according to claim 1, wherein said peripheral surface portion is formed integrally with or separately from said body portion and said body portion has a chemical composition different from that of said peripheral surface portion.

7. The method according to claim 6, wherein said peripheral surface portion comprises a polymer containing nonionic hydrophilic groups and nitrogen-containing basic functional groups, and has a basic nitrogen atom content of from 0.2 to 4.0% by weight, said peripheral surface portion being comprised of a coating formed on said body portion having a chemical composition different from that of said polymer.

8. The method according to claim 6, wherein said peripheral surface portion is formed integrally with said body portion.

9. The method according to any one of claims 1 to 3, wherein the basic nitrogen atom content of said peripheral surface portion is from 0.3 to 1.5% by weight.

10. The method according to claim 1, wherein said peripheral surface portion is formed integrally with said body portion, and each of said body portion and said peripheral surface portion contains nonionic hydrophilic groups and nitrogen-containing basic functional groups and has a basic nitrogen atom content of from 0.2 to 4.0% by weight.

11. The method according to claim 1, wherein said nonionic hydrophilic group is a hydroxyl group, an amide group, a polyethylene oxide chain or mixtures thereof, and said nitrogen-containing basic functional group is a primary amino group, a secondary amino group, a tertiary amino group, a quaternary ammonium group, a nitrogen-containing aromatic ring group or mixtures thereof.

12. The method according to claim 1, wherein said vinyl monomer having a nonionic hydrophilic group is selected from the group consisting of 2-hydroxyethyl(meth)acrylate, 2-hydroxypropyl(meth)acrylate, vinyl alcohol, (meth)acrylamide, N-vinyl pyrrolidone and monomethoxy polyethylene glycol methacrylate.

13. The method according to claim 1, wherein said vinyl monomer having a nitrogen-containing basic functional group is selected from vinyl compounds of the group consisting of allylamine, (meth)acrylic acid derivatives, styrene derivatives and vinyl derivatives of nitrogen-containing aromatic compounds, and from derivatives obtained by converting said vinyl compounds to quaternary ammonium salts.

14. A filter medium for selectively removing leucocytes, which comprises a plurality of fibers, each comprising
   a body portion and a peripheral surface portion, at least said peripheral surface portion of which comprises a polymer obtained by polymerization of at least one vinyl monomer having a nonionic hydrophilic group with at least one vinyl monomer having a nitrogen-containing basic functional group and has a basic nitrogen atom content of from 0.2 to 4.0% by weight,
   said filter medium being for use in collecting a substantially leucocyte free, platelet-enriched suspension from a suspension containing leucocytes and platelets, said collected platelet-enriched suspension being adapted to be used for platelet transfusion or to be returned to a donor of said suspension containing leucocytes and platelets for performing extracorporeal leucocyte removal therapy.

15. A filter medium according to claim 14, wherein each fiber has a diameter of from 10 μm or less.

16. The filter medium according to claim 14, wherein each fiber has a diameter of from 0.3 μm to less than 3.0 μm.

17. The filter medium according to any one of claims 14 to 16, which is in the form of a non-woven fabric.

18. The filter medium according to any one of claims 14 to 16, wherein said peripheral surface portion is formed integrally with or separately from said body portion and said body portion has a chemical composition different from that of said peripheral surface portion.

19. The filter medium according to claim 18, wherein said peripheral surface portion comprises a polymer containing nonionic hydrophilic groups and nitrogen-containing basic functional groups, and has a basic nitrogen atom content of from 0.2 to 4.0% by weight, said peripheral surface portion being comprised of a coating formed on said body portion having a chemical composition different from that of said polymer.

20. The filter medium according to claim 18, wherein said peripheral surface portion is formed integrally with said body portion.

21. The filter medium according to any one of claims 14 to 16, wherein the basic nitrogen atom content of said peripheral surface portion which contains nonionic hydrophilic groups and nitrogen-containing basic functional groups is from 0.3 to 1.5% by weight.

22. The filter medium according to claim 14, wherein said peripheral surface portion is formed integrally with said body portion, and each of said body portion and said peripheral surface portion contains nonionic hydrophilic groups and nitrogen-containing basic functional groups and has a basic nitrogen atom content of from 0.2 to 4.0% by weight.

23. The filter medium according to claim 14, wherein said nonionic hydrophilic group is a hydroxyl group, an amide group, a polyethylene oxide chain or mixtures thereof, and said nitrogen-containing basic functional group is a primary amino group, a secondary amino group, a tertiary amino group, a quaternary ammonium group, a nitrogen-containing aromatic ring group or mixtures thereof.

24. The filter medium according to claim 14, wherein said vinyl monomer having a nonionic hydrophilic group is selected from the group consisting of 2-hydroxyethyl(meth)acrylate, 2-hydroxypropyl(meth)acrylate, vinyl alcohol, (meth)acrylamide, N-vinyl pyrrolidone and monomethoxy polyethylene glycol methacrylate.

25. The filter medium according to claim 14, wherein said vinyl monomer having a nitrogen-containing basic functional group is selected from vinyl compounds of the group consisting of allylamine, (meth)acrylic acid derivatives, styrene derivatives and vinyl derivatives of nitrogen-containing aromatic compounds, and from derivatives obtained by converting said vinyl compounds to quaternary ammonium salts.

26. The filter medium according to claim 14, wherein the basic nitrogen atom content of said peripheral surface portion is from 0.2 to 1.5% by weight.

* * * * *